United States Patent [19]
Weiss et al.

[11] Patent Number: 6,165,783
[45] Date of Patent: Dec. 26, 2000

[54] ERYTHROPOIETIN-MEDIATED NEUROGENESIS

[75] Inventors: Samuel Weiss, Calgary; S. Todd Sorokan, Victoria, both of Canada

[73] Assignee: Neuro Spheres Holdings Ltd., Calgary, Canada

[21] Appl. No.: 09/175,890

[22] Filed: Oct. 20, 1998

Related U.S. Application Data

[60] Provisional application No. 60/063,040, Oct. 24, 1997.

[51] Int. Cl.$^7$ ........................................ C12N 5/00
[52] U.S. Cl. .................... 435/325; 435/367; 435/378; 435/375; 514/2; 424/85.1
[58] Field of Search ................... 435/325, 368, 435/377, 375; 514/2; 424/85.1

[56] References Cited

U.S. PATENT DOCUMENTS 5,750,376  5/1998  Weiss et al. .................. 435/69.52

FOREIGN PATENT DOCUMENTS

| | | |
|---|---|---|
| WO93/01275 | 1/1993 | WIPO . |
| WO94/10292 | 5/1994 | WIPO . |
| WO95/03821 | 2/1995 | WIPO . |
| WO95/13364 | 5/1995 | WIPO . |
| WO 96/15226 | 5/1996 | WIPO . |

OTHER PUBLICATIONS

Masuda et al. The Journal of Biological Chemistry. 269(30). 19488–19493, 1994.
Masuda et al. Brain Research. 746. 63–70, 1997.
Bauer. J. Perinat. Med. 23 7–12, 195.
Bauer, C., "Upregulation of erythropoietin by hypoxia in the brain of mammals", *Wiener Klinische Wochenschrift* 109: 535 (1997).
Digicaylioglu, M. et al., "Localization of specific erythropoietin binding sites in defined areas of the mouse brain", *Proc. Nat'l. Acad. Sci.* 92: 3717–3720 (1995).
Juul, S.E. and R.D. Christensen, "Erythropoietin (EPO) may promote neuronal suvival following hypoxia, by repressing apoptosis", *Pediatric Research* 41: 291A (1997).
Juul, S.E. et al., "Erythropoietin and erythropoiein receptor in the developing human central nervous system", *Pediatric Research* 43: 40–49 (1998).
Marti, H.H. et al., "Detection of erythropoietin in human liquor: intrinsic erythropoietin production in the brain", *Kidney Int'l* 51:416–418 (1997).
Sorokan, T. and S. Weiss, "Effects of hypoxia on neuronal production from embryonic murine CNS stem cells", *Mol. Bio. of the Cell* 7 (supp): 371A (1996).
Srolkan, T. and S. Weiss, "Erythropoietin mediates increased neurogenesis by embryonic CNS stem cells following a modes hypoxic insult", *Society For Neurosciences Abstracts* 23: 320 (1997).
Weiss, S. et al., "Is there a nerual stem cell in the mammalian forebrain?", *Trends in Neurosciences* 19: 387–393 (1996).
Bayer, Shirley A., "Neuron Production in the Hippocampus and Olfactory Bulb of the Adult Rat Brain: Addition or Replacement?", *Annals N.Y. Acad. Sci.*, 457:163–173 (1985).
Freed, Curt R., et al., "Survival of Implanted Fetal Dopamine Cells and Neurologic Improvement 12 to 46 Months After Transplantation for Parkinson's Disease", *N. Eng. J. Med.*, 327(22):1549–1555 (1992).
Kaplan, Michael S., "Neurogenesis in the 3–Month–Old Rat Visual Cortex", *J. Comp. Neuro.*, 195:323–338 (1981).
Perlow, Mark J., et al., "Brain Grafts Reduce Motor Abnormalities Produced by Destruction of Nigrostriatal Dopamine System", *Sci.*, 204:643–647 (May 1979).
Potten, C.S., et al., "Stem cells: attributes, cycles, spirals, pitfalls and uncertainties. Lessons for and from the Crypt", *Dev.*, 110:1001–1020 (1990).
Rakic, Pasko, "Limits of Neorogenesis in Primates", *Sci.*, 227:1054–1056 (Mar. 1985).
Reynolds, Brent A., et al., "Generation of Neurons and Astrocytes from Isolated Cells of the Adult Mammalian Central Nervous System", *Sci.*, 255:1707–1710 (Mar. 1992).
Spencer, Dennis D., et al., "Unilateral Transplantation of Human Fetal Mesencephalic Tissue Into the Caudate Nucleus of Patients with Parkinson's Disease", *N. Eng. J. Med.*, 327(22):1541–1548 (Nov. 1992).
Widner, Hakan, et al., "Bilateral Fetal Mesencephalic Grafting in Two Patients with Parkinsonism Induced by 1–Methyl–4–Phenyl–1,2,3,6–Tetrahydropyridine (MPTP)", *N. Eng. J. Med.*, 327(22):1556–1563 (Nov. 1992).

*Primary Examiner*—Leon B. Lankford, Jr.
*Attorney, Agent, or Firm*—Burns Doane Swecker & Mathis LLP

[57] ABSTRACT

Methods are described for the production of neurons or neuronal progenitor cells. Multipotent neural stem cells are proliferated in the presence of growth factors and erythropoietin which induces the generation of neuronal progenitor cells. The erythropoietin may be exogenously applied to the multipotent neural stem cells, or alternatively, the cells can be subjected to hypoxic insult which induces the cells to express erythropoietin.

12 Claims, No Drawings

ERYTHROPOIETIN-MEDIATED NEUROGENESIS

This application claims benefit to provisional application 60/063,040 filed Oct. 24, 1997.

FIELD OF THE INVENTION

This invention relates to methods of influencing multipotent neural stem cells to produce progeny that differentiate into neurons by exposing the stem cells and their progeny to erythropoietin.

BACKGROUND OF THE INVENTION

Neurogenesis in mammals is complete early in the postnatal period. Cells of the adult mammalian CNS have little or no ability to undergo mitosis and generate new neurons. While a few mammalian species (e.g. rats) exhibit the limited ability to generate new neurons in restricted adult brain regions such as the dentate gyrus and olfactory bulb (Kaplan, J. Comp. Neurol., 195:323, 1981; Bayer, N.Y. Acad. Sci., 457:163, 1985), the generation of new CNS neurons in adult primates does not normally occur (Rakic, Science, 227:1054, 1985). This inability to produce new nerve cells in most mammals (and especially primates) may be advantageous for long-term memory retention; however, it is a distinct disadvantage when the need to replace lost neuronal cells arises due to injury or disease.

The role of stem cells in the adult is to replace cells that are lost by natural cell death, injury or disease. Until recently, the low turnover of cells in the mammalian CNS together with the inability of the adult mammalian CNS to generate new neuronal cells in response to the loss of cells following injury or disease had led to the assumption that the adult mammalian CNS does not contain multipotent neural stem cells. The critical identifying feature of a stem cell is its ability to exhibit self-renewal or to generate more of itself. The simplest definition of a stem cell would be a cell with the capacity for self-maintenance. A more stringent (but still simplistic) definition of a stem cell is provided by Potten and Loeffler (Development, 110:1001, 1990) who have defined stem cells as "undifferentiated cells capable of a) proliferation, b) self-maintenance, c) the production of a large number of differentiated functional progeny, d) regenerating the tissue after injury, and e) a flexibility in the use of these options."

CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). Degeneration in a brain region known as the basal ganglia can lead to diseases with various cognitive and motor symptoms, depending on the exact location. The basal ganglia consists of many separate regions, including the striatum (which consists of the caudate and putamen), the globus pallidus, the substantia nigra, substantia innominate, ventral pallidum, nucleus basalis of Meynert, ventral tegmental area and the subthalamic nucleus. Many motor deficits are a result of neuronal degeneration in the basal ganglia. Huntington's Chorea is associated with the degeneration of neurons in the striatum, which leads to involuntary jerking movements in the host. Degeneration of a small region called the subthalamic nucleus is associated with violent flinging movements of the extremities in a condition called ballismus, while degeneration in the putamen and globus pallidus is associated with a condition of slow writhing movements or athetosis. Other forms of neurological impairment can occur as a result of neural degeneration, such as cerebral palsy, or as a result of CNS trauma, such as stroke and epilepsy.

In recent years neurodegenerative disease has become an important concern due to the expanding elderly population which is at greatest risk for these disorders. These diseases, which include Alzheimer's Disease and Parkinson's Disease, have been linked to the degeneration of neuronal cells in particular locations of the CNS, leading to the inability of these cells or the brain region to carry out their intended function. In the case of Alzheimer's Disease, there is a profound cellular degeneration of the forebrain and cerebral cortex. In addition, upon closer inspection, a localized degeneration in an area of the basal ganglia, the nucleus basalis of Meynert, appears to be selectively degenerated. This nucleus normally sends cholinergic projections to the cerebral cortex which are thought to participate in cognitive functions including memory. In the case of Parkinson's Disease, degeneration is seen in another area of the basal ganglia, the substantia nigra par compacta. This area normally sends dopaminergic connections to the dorsal striatum which are important in regulating movement. Therapy for Parkinson's Disease has centered upon restoring dopaminergic activity to this circuit through the use of drugs.

In addition to neurodegenerative diseases, acute brain injuries often result in the loss of neurons, the inappropriate functioning of the affected brain region, and subsequent behavior abnormalities.

To date, treatment for CNS disorders has been primarily via the administration of pharmaceutical compounds. Unfortunately, this type of treatment has been fraught with many complications including the limited ability to transport drugs across the blood-brain barrier and the drug-tolerance which is acquired by patients to whom these drugs are administered long-term. For instance, partial restoration of dopaminergic activity in Parkinson's patients has been achieved with levodopa, which is a dopamine precursor able to cross the blood-brain barrier. However, patients become tolerant to the effects of levodopa, and therefore, steadily increasing dosages are needed to maintain its effects. In addition, there are a number of side effects associated with levodopa such as increased and uncontrollable movement.

Recently, the concept of neurological tissue grafting has been applied to the treatment of neurological diseases such as Parkinson's Disease. Neural grafts may avert the need not only for constant drug administration, but also for complicated drug delivery systems which arise due to the blood-brain barrier. However, there are limitations to this technique as well. First, cells used for transplantation which carry cell surface molecules of a differentiated cell from another host can induce an immune reaction in the host. In addition, the cells must be at a stage of development where they are able to form normal neural connections with neighboring cells. For these reasons, initial studies on neurotransplantation centered on the use of fetal cells. Several studies have shown improvements in patients with Parkinson's Disease after receiving implants of fetal CNS tissue. Implants of embryonic mesencephalic tissue containing dopamine cells into the caudate and putamen of human patients was shown by Freed et al. (*N Engl J Med* 327:1549–1555 (1992)) to offer long-term clinical benefit to some patients with advanced Parkinson's Disease. Similar success was shown by Spencer et al. (*N Engl J Med* 327:1541–1548 (1992)). Widner et al. (*N Engl J Med* 327:1556–1563 (1992)) have shown long-term functional improvements in patients with MPTP-induced Parkinsonism that received bilateral implantation of fetal mesencephalic tissue. Perlow, et al. describe the transplantation of fetal dopaminergic neurons into adult rats with chemically induced nigrostriatal lesions in "Brain grafts reduce motor abnormalities produced by destruction of nigrostriatal dopamine system," Science 204:643–647 (1979). These grafts showed good survival, axonal outgrowth and significantly reduced the motor abnormalities in the host animals.

While the studies noted above are encouraging, the use of large quantities of aborted fetal tissue for the treatment of disease raises ethical considerations and political obstacles. There are other considerations as well. Fetal CNS tissue is composed of more than one cell type, and thus is not a well-defined source of tissue. In addition, there are serious doubts as to whether an adequate and constant supply of fetal tissue would be available for transplantation. For example, in the treatment of MPTP-induced Parkinsonism (Widner supra) tissue from 6 to 8 fresh fetuses were required for implantation into the brain of a single patient. There is also the added problem of the potential for contamination during fetal tissue preparation. Moreover, the tissue may already be infected with a bacteria or virus, thus requiring expensive diagnostic testing for each fetus used. However, even diagnostic testing might not uncover all infected tissue. For example, the diagnosis of HIV-free tissue is not guaranteed because antibodies to the virus are generally not present until several weeks after infection.

While currently available transplantation approaches represent a significant improvement over other available treatments for neurological disorders, they suffer from significant drawbacks. The inability in the prior art of the transplant to fully integrate into the host tissue, and the lack of availability of neuronal cells in unlimited amounts from a reliable source for grafting are, perhaps, the greatest limitations of neurotransplantation. A well-defined, reproducible source of neural cells has recently been made available. It has been discovered that multipotent neural stem cells, capable of producing progeny that differentiate into neurons and glia, exist in adult mammalian neural tissue. (Reynolds and Weiss, Science 255:1707 (1992)). Methods have been provided for the proliferation of these stem cells to provide large numbers of neural cells that can differentiate into neurons and glia (See. U.S. Pat. No. 5,750,376, and International Application No. WO 93/01275). Various factors can be added to neural cell cultures to influence the make-up of the differentiated progeny of multipotent neural stem cell progeny, as disclosed in published PCT application WO 94/10292. Additional methods for directing the differentiation of the stem cell progeny would be desirable.

SUMMARY OF THE INVENTION

A method of producing neurons or neuronal progenitor cells which can be used for transplantation or other purposes is described. The method comprises inducing multipotent neural stem cells to produce neuronal progenitor cells by proliferating the multipotent neural stem cells in the presence of growth factors and erythropoietin. The erythropoietin may originate from the population of neural cells by subjecting the cells to hypoxic insult which induces neural cells to express erythropoietin. Alternatively, the erythropoietin may be provided exogenously.

DETAILED DESCRIPTION OF THE INVENTION

As used herein, the term multipotent or oligopotent neural stem cell refers to an undifferentiated cell which is capable of self-maintenance. Thus, in essence, a stem cell is capable of dividing without limit. The non-stem cell progeny of a multipotent neural stem cell are termed "progenitor cells." A distinguishing feature of a progenitor cell is that, unlike a stem cell, it has limited proliferative ability and thus does not exhibit self-maintenance. It is committed to a particular path of differentiation and will, under appropriate conditions, eventually differentiate. A neuronal progenitor cell is capable of a limited number of cell divisions before giving rise to differentiated neurons. A glial progenitor cell likewise is capable of a limited number of cell divisions before giving rise to astrocytes or oligodendrocytes. A neural stem cell is multipotent because its progeny include both neuronal and glial progenitor cells and thus is capable of giving rise to neurons, astrocytes, and oligodendrocytes.

Various factors can be added to neural cell cultures to influence the make-up of the differentiated progeny of multipotent neural stem cell progeny, as disclosed in WO 94/10292. It has now been found that erythropoietin (EPO), a hormone thought to influence the differentiative pathway of hematopoietic stem cells and/or their progeny, can increase the number of neuronal progeny that are generated from proliferated multipotent neural stem cells. Multipotent neural stem cells proliferated in the presence of EPO produce a greater percentage of neuronal progenitor cells than multipotent neural stem cells proliferated in the absence of EPO.

Multipotent neural stem cells can be obtained from embryonic, juvenile, or adult mammalian neural tissue (e.g. mouse and other rodents, and humans and other primates) and can be induced to proliferate in vitro or in vivo using the methods disclosed in published PCT application WO 93/01275 and U.S. Pat. No. 5,750,376. Briefly, the administration of one or more growth factors can be used to induce the proliferation of multipotent neural stem cells. Preferred proliferation-inducing growth factors include epidermal growth factor (EGF), amphiregulin, acidic fibroblast growth factor (aFGF or FGF-1), basic fibroblast growth factor (bFGF or PGF-2), transforming growth factor alpha (TGFα), and combinations thereof. For the proliferation of multipotent neural stem cells in vitro, neural tissue is dissociated and the primary cell cultures are cultured in a suitable culture medium, such as the serum-free defined medium described in Example 1. A suitable proliferation-inducing growth factor, such as EGF (20 ng/ml) is added to the culture medium to induce multipotent neural stem cell proliferation.

In the absence of substrates that promote cell adhesion (e.g. ionically charged surfaces such as poly-L-lysine and poly-L-ornithine coated and the like), multipotent neural stem cell proliferation can be detected by the formation of clusters of undifferentiated neural cells termed "neurospheres", which after several days in culture, lift off the floor of the culture dish and float in suspension. Each neurosphere results from the proliferation of a single multipotent neural stem cell and is comprised of daughter multipotent neural stem cells and neural progenitor cells. The neurospheres can be dissociated to form a suspension of undifferentiated neural cells and transferred to fresh growth-factor containing medium. This re-initiates proliferation of the stem cells and the formation of new neurospheres. In this manner, an unlimited number of undifferentiated neural stem cell progeny can be produced by the continuous culturing and passaging of the cells in suitable culture conditions.

Various procedures are disclosed in WO 94/10292 and U.S. Pat. No. 5,750,376 which can be used to induce the proliferated neural stem cell progeny to differentiate into neurons, astrocytes and oligodendrocytes. To increase the number of neuronal progenitor cells that are produced by the multipotent neural stem cells, the proliferating stem cells can be exposed to EPO. The EPO can be exogenously added at concentrations from about 0.1 to 10 units/ml. Alternatively, the neural cells can be induced to express endogenous EPO by subjecting the cells to hypoxic insult. Subsequent differentiation of the progenitor cell progeny results in at least a two-fold increase in the numbers of neurons generated compared to progeny of stem cells that have not been exposed to EPO, as evidenced by imnmunocytochemical analysis. Differentiation of cells that have not been exposed to endogenously added EPO or hypoxic insult typically results in a population of cells containing about 3% neurons. The percentage of neurons increases to about 6% with hypoxia treatment, and to about 10% with exposure to exogenous EPO, with the percentage of astrocytes and oligodendrocytes remaining about the same as the control populations.

Washout experiments, in which the growth factor/EPO medium is removed after 24 hours and changed to regular growth factor-containing medium, reveals that the EPO instructs the stem cells prior to their first cell division, to produce more neurons. The continued presence of EPO after the initial 24 hours does not result in a further increase in the numbers of neurons over cultures subjected to EPO for a 24 hour period.

The ability to manipulate the fate of the differentiative pathway of the multipotent neural stem cell progeny to produce more neuronal progenitor cells and neurons is beneficial. Cell cultures that contain a higher percentage of neuronal progenitor cells and/or neurons will be useful for screening the effects of various drugs and other agents on neuronal cells. Methods for screening the effect of drugs on cell cultures are well known in the art and are also disclosed in U.S. Pat. No. 5,750,376.

Cell cultures with an enriched neuronal-progenitor cell and/or neuron population can be used for transplantation to treat various neurological injuries, diseases or disorders. The neuronal progenitor cells or neurons or a combination thereof can be harvested and transplanted into a patient needing neuronal augmentation. Neuronal progenitor cells are particularly suitable for transplantation because they are still undifferentiated and, unlike differentiated neurons, there are no branched processes which can be damaged during transplantation procedures. Once transplanted, the neuronal progenitor cells differentiate in situ into new, functioning neurons. Suitable transplantation methods are known in the art and are disclosed in U.S. Pat. No. 5,750,376.

Alternatively, a patient's endogenous multipotent neural stem cells could be induced to proliferate in situ to produce neuronal progenitor cells by administering to the patient a composition comprising one or more growth factors which induces the patient's neural stem cells to proliferate and EPO which instructs the proliferating neural stem cells to produce neuronal progenitor cells which eventually differentiate into neurons. Suitable methods for administering a composition to a patient which induces the in situ proliferation of the patient's stem cells are disclosed in U.S. Pat. No. 5,750,376.

All cited references, patents and applications are herein incorporated in their entireties by reference.

EXAMPLE 1
Multipotent neural stem cell proliferation

Striata from 14-day-old mouse embryos were removed using sterile procedure. Tissue was mechanically dissociated into serum-free medium composed of a 1:1 mixture of Dulbecco's modified Eagle's medium (DMEM) and F-12 nutrient (Gibco). Dissociated cells were centrifuged, the supernatant aspirated, and the cells resuspended at a concentration of about $1 \times 10^5$ cell/ml in a serum-free medium, referred to herein as "complete medium" composed of DMEM/F-12 (1:1) including glucose (0.6%), glutamine (2 $\mu$M), sodium bicarbonate (3 mM), and HEPES (4-[2hydroxyethyl]-1-piperazineethanesulfonic acid) buffer (5 mM) (all from Sigma except glutamine [Gibco]). A defined hormone mix and salt mixture (Sigma) that included insulin (25 $\mu$g/ml), transferrin (100 $\mu$g/ml), progesterone (20 nM), putrescine (60 $\mu$M), and selenium chloride (30 nM) was used in place of serum. The complete medium was supplemented with 20 ng/ml of EGF (Collaborative Research). Cells were seeded in a T25 culture flask and housed in an incubator at 37° C., 100% humidity, 95% air/5% $CO_2$. Stem cells within the cultures began to proliferate within 3–4 days and due to a lack of substrate lifted off the floor of the flask and continued to proliferate in suspension forming neurospheres.

EXAMPLE 2
Hypoxia-induced neurogenesis

After 6 days in vitro primary neurospheres formed using the methods described in Example 1 were dissociated and were replated in EGF-containing medium. After 24 hours, the cells were exposed to a modest hypoxic insult by decreasing the concentration of oxygen in the culture medium for varying lengths of time (from 1 to 12 hours) from normal levels of 135 mmHg to 30–40 mmHg. The cells were then cultured in the EGF-containing complete medium described in Example 1 in 95% air/5% $CO_2$ for 7 days. Hypoxia did not prevent multipotent neural stem cell proliferation, as evidenced by the formation of secondary neurospheres. The number of progeny produced from hypoxia-treated stem cells was the same as that in control cultures not subjected to hypoxic insult.

Secondary neurospheres generated from untreated or hypoxia-treated stem cells were dissociated into single cells and induced to differentiate by plating between $0.5 \times 10^6$ and $1.0 \times 10^6$ cells onto poly-L-ornithine-coated (15 $\mu$g/ml) glass coverslips in 24 well Nuclon (1.0 ml/well) culture dishes in EGF-free complete medium optionally supplemented with 1% FBS. After 7 days, the cells were assayed using immunocytochemical analysis for the presence of neurons. Cultures that had been subjected to hypoxic conditions for 1 to 4 hours had approximately a two-fold increase in the percentage of neurons (approx. 6%) over control cultures (approx. 3%). Cultures subjected to 4 to 8 hours of hypoxia had fewer neurons produced and cultures subjected to about 12 hours of hypoxia had normal levels (approx. 3%). The hypoxic insult induced a rapid up-regulation of hypoxia-induced factor (HIF) in the multipotent neural stem cell progeny. HIP is a transcription factor for EPO. The 4-hour hypoxia-induced increase in neurogenesis could be blocked by the addition of an EPO-neutralizing antibody at 3 $\mu$g/ml.

EXAMPLE 3
Erythropoietin-induced neurogenesis

After 6 days in vitro primary neurospheres formed using the methods described in Example 1 were dissociated and replated in complete medium containing EGF at 20 ng/ml and human recombinant EPO at 0.1 to 10 units/ml for either 24 hours or 7 days under normal oxygen conditions (95% air/5% $CO_2$; 135 mmHg). In both cases, immunocytochemistry revealed an EPO dose-dependent three-fold increase in the numbers of neurons generated.

What is claimed is:

1. A method of inducing the differentiation of multipotent neural stem cells into neurons, said method comprising the steps of:
    (a) inducing said multipotent neural stem cells to proliferate;
    (b) contacting said multipotent neural stem cells with an exogenously added amount of erythropoietin effective to cause said multipotent neural stem cells and their progeny to produce neuronal progenitor cells; and
    (c) allowing said neuronal progenitor cells to differentiate into neurons.

2. The method of claim 1 wherein at least one exogenously added growth factor induces said multipotent neural stem cells to proliferate.

3. The method of claim 2 wherein said exogenously added growth factor is epidermal growth factor.

4. The method of claim 1 wherein step (b) is performed after step (a).

5. The method of claim 1 wherein steps (a) and (b) are performed concurrently.

6. A method of treating a neurodegenerative disease or an acute brain injury in a mammal by producing neurons from multipotent neural stem cells comprising inducing said multipotent neural stem cells to differentiate into neurons in the presence of exogenously added erythropoietin.

7. The method of claim 6 wherein said erythropoietin is administered into said mammal in an amount sufficient to induce the differentiation of the endogenous multipotent neural stem cells of said mammal into neurons.

8. The method of claim 7 further comprising the administration of at least one other growth factor which induces the multipotent neural stem cells to proliferate.

9. The method of claim 8 wherein said at least one other growth factor is epidermal growth factor.

10. The method of claim 6 wherein said multipotent neural stem cells and/or progenitor cells which are derived from said multipotent neural stem cells are transplanted into said mammal.

11. The method of claim 10 wherein said multipotent neural stem cells and/or progenitor cells are incubated with erythropoietin and at least one other growth factor before being transplanted into said mammal.

12. The method of claim 11 wherein said at least one other growth factor is epidermal growth factor.

* * * * *